(12) United States Patent
Decoux et al.

(10) Patent No.: US 9,465,367 B2
(45) Date of Patent: Oct. 11, 2016

(54) METHOD AND SYSTEM FOR AUTHENTICATING USING EXTERNAL EXCITATION

(71) Applicant: SICPA HOLDING SA, Prilly (CH)

(72) Inventors: Eric Decoux, Vevey (CH); Lorenzo Sirigu, Lausanne (CH); Andrea Callegari, Chavannes-près-Renens (CH); Yves Berthier, Metabief (FR)

(73) Assignee: SICPA HOLDING SA, Prilly (CH)

( * ) Notice: Subject to any disclaimer, the term of this patent is extended or adjusted under 35 U.S.C. 154(b) by 430 days.

(21) Appl. No.: 13/940,709

(22) Filed: Jul. 12, 2013

(65) Prior Publication Data

US 2014/0013846 A1    Jan. 16, 2014

Related U.S. Application Data

(60) Provisional application No. 61/739,392, filed on Dec. 19, 2012, provisional application No. 61/739,381, filed on Dec. 19, 2012.

(30) Foreign Application Priority Data

Jul. 13, 2012  (EP) ..................................... 12005180
Jul. 13, 2012  (EP) ..................................... 12005181

(51) Int. Cl.
*G04D 7/00* (2006.01)
*G04D 7/12* (2006.01)
(Continued)

(52) U.S. Cl.
CPC .............. *G04D 7/1214* (2013.01); *G01M 7/00* (2013.01); *G01N 21/87* (2013.01); *G04B 47/042* (2013.01);
(Continued)

(58) Field of Classification Search
CPC .. G04D 7/1214; G04D 7/1207; G04D 7/004; G04D 7/005; G04D 7/1228; G04D 7/125
USPC ........................ 73/579, 1.43, 1.46, 1.48, 1.49
See application file for complete search history.

(56) References Cited

U.S. PATENT DOCUMENTS 2,782,627 A * 2/1957 Hetzel .................. G04D 7/1214
                                                73/1.48
3,690,144 A * 9/1972 Bonny ........................... 73/1.51
(Continued)

FOREIGN PATENT DOCUMENTS

CH          694 111 A5     7/2004
DE       103 38932 A1      3/2005
(Continued)

OTHER PUBLICATIONS

M. Disher, "An Overview of the COSC Certificate and Testing Procedures," pp. 1-4, dated Feb. 12, 2000.
(Continued)

*Primary Examiner* — Helen Kwok
(74) *Attorney, Agent, or Firm* — Greenblum & Bernstein, P.L.C.

(57) ABSTRACT

Method for authenticating a timepiece including applying at least one external excitation to said timepiece using an external device, measuring acoustic vibrations at least one of emitted and absorbed inside the timepiece to obtain an electrical signal representative of the measured acoustic vibrations, wherein a magnitude of the electrical signal represents magnitude information of the measured acoustic vibrations as a function of time, comparing the magnitude information with at least one reference magnitude information, and determining an authenticity of the timepiece based on the comparing.

31 Claims, 10 Drawing Sheets

(51) Int. Cl.
 *G01M 7/00* (2006.01)
 *G01N 21/87* (2006.01)
 *G04B 47/04* (2006.01)

(52) U.S. Cl.
 CPC .............. *G04D 7/001* (2013.01); *G04D 7/002* (2013.01); *G04D 7/004* (2013.01); *G04D 7/005* (2013.01); *G04D 7/1228* (2013.01)

(56) References Cited

U.S. PATENT DOCUMENTS

| | | | |
|---|---|---|---|
| 3,756,066 A | | 9/1973 | Bolliger |
| 3,811,315 A | * | 5/1974 | Kunitomi ..................... 73/1.48 |
| 3,817,083 A | * | 6/1974 | Jucker ......................... 73/1.43 |
| 3,864,957 A | * | 2/1975 | Fujita ........................... 73/1.48 |
| 3,892,124 A | * | 7/1975 | Reese .......................... 73/1.44 |
| 3,946,592 A | * | 3/1976 | Ichikawa et al. ............. 73/1.48 |
| 4,012,941 A | | 3/1977 | Jucker |
| 4,024,750 A | * | 5/1977 | Erickson ....................... 73/1.52 |
| 4,028,927 A | | 6/1977 | Kikuyama et al. |
| 4,078,419 A | | 3/1978 | Busch et al. |
| 4,078,420 A | | 3/1978 | Reese |
| 4,083,222 A | * | 4/1978 | Stawiski ........................ 73/1.43 |
| 4,224,820 A | * | 9/1980 | Sitkewich et al. ............. 73/1.49 |
| 4,320,529 A | | 3/1982 | Maeda |
| 4,452,082 A | | 6/1984 | Miwa |
| 5,572,488 A | * | 11/1996 | Yamada et al. ................. 368/10 |
| 5,619,616 A | | 4/1997 | Brady et al. |
| 7,057,430 B2 | | 6/2006 | Ogiso |
| 7,605,372 B2 | | 10/2009 | Hachin |
| 7,979,731 B2 | | 7/2011 | Futa |
| 2003/0112708 A1 | * | 6/2003 | Fujisawa et al. ................. 368/47 |
| 2004/0113819 A1 | * | 6/2004 | Gauthey et al. ................. 341/34 |
| 2006/0293606 A1 | | 12/2006 | Tomita |
| 2009/0278670 A1 | * | 11/2009 | Karapatis et al. ........... 340/393.4 |
| 2011/0110200 A1 | * | 5/2011 | Goeller ......................... 368/243 |
| 2013/0170327 A1 | * | 7/2013 | Peters et al. ..................... 368/62 |
| 2014/0013847 A1 | * | 1/2014 | Decoux et al. .................. 73/579 |
| 2014/0019089 A1 | * | 1/2014 | Decoux et al. ............... 702/178 |
| 2015/0013460 A1 | | 1/2015 | Favre |
| 2015/0053006 A1 | * | 2/2015 | Decoux et al. .................. 73/579 |
| 2015/0053007 A1 | * | 2/2015 | Decoux et al. .................. 73/579 |
| 2015/0309478 A1 | * | 10/2015 | Decoux ................... G04D 7/001 73/648 |

FOREIGN PATENT DOCUMENTS

| | | |
|---|---|---|
| EP | 0 072 350 A1 | 2/1983 |
| EP | 1 021 790 A1 | 7/2000 |
| FR | 2 957 689 A1 | 9/2011 |
| JP | 05264335 | 10/1993 |
| JP | 2010259629 | 11/2010 |
| WO | WO99/19831 A1 | 4/1999 |
| WO | WO99/21061 A1 | 4/1999 |

OTHER PUBLICATIONS

Search Report and Written Opinion in related International Application No. PCT/EP2013/064865, dated Aug. 21, 2013.

* cited by examiner

METHOD AND SYSTEM FOR AUTHENTICATING USING EXTERNAL EXCITATION

CROSS REFERENCE TO RELATED APPLICATIONS

The present application claims priority to European Patent Application Nos. 12005181.8 and 12005180.0 filed on Jul. 13, 2012, and claims the benefit of U.S. Provisional Application Nos. 61/739,392 and 61/739,381, filed on Dec. 19, 2012, the disclosures of which are expressly incorporated by reference herein in their entireties.

FIELD OF THE INVENTION

Embodiments of the present invention relates to a method and system for authenticating an object or device using external excitation.

BACKGROUND OF THE INVENTION

Counterfeit consumer goods, commonly called knock-offs, are counterfeit or imitation products offered for sale. The spread of counterfeit goods has become global in recent years and the range of goods subject to counterfeiting has increased significantly.

Watches are vulnerable to counterfeiting, and have been counterfeited for decades. A counterfeit watch is an unauthorized copy of a part or all of an authentic watch. According to estimates by the Swiss Customs Service, there are some 30 to 40 million counterfeit watches put into circulation each year. It is a common cliché that visitors to New York City are approached on the street by vendors with a dozen such counterfeit watches inside their coats, offered at bargain prices. A counterfeit product may look genuine from the outside and contain sub-standard components. Extremely authentic looking, but very poor quality counterfeit watches can sell for as little as twenty dollars. The problem is becoming more and more serious, with the quality of the counterfeits constantly increasing.

Authentication solutions that have been used for protection of consumer goods from counterfeiting are often based on marking the item with a specific material, code, or marking, engraving, etc. However, these methods modify the nature and the appearance of the object, and this is often not acceptable in the watch (and other luxury items) industry, where the design of the object and its visual appearance are of paramount importance. Additionally, outer marks may be exposed to copy and environmental factors (wear, dirt, etc.). Also, these methods require an active intervention at the time of manufacturing or distribution and, correspondingly, an important change of the production process.

It is desirable, when assessing the authenticity of a timepiece, to have as much information as possible not only on its outer appearance but also on its inner content. It is furthermore desirable not to have to open the timepiece when checking the authenticity, as the operation requires specialized equipment and procedures, which may impact the performance and/or integrity of the piece (e.g., water tightness), and which may invalidate the manufacturer's warranty.

It is, therefore, desirable to be able to authenticate a timepiece in a manner that is as non-invasive and as reliable as possible without having to open the timepiece.

SUMMARY OF EMBODIMENTS OF THE INVENTION

An aim of the invention is to provide a method for authenticating a timepiece that is non-invasive and reliable.

This aim is solved by the subject matter of the independent claims. Preferred embodiments are subject matter of the dependent claims.

One embodiment of the invention provides a method for authenticating a timepiece. The method includes applying at least one external excitation to the timepiece using an external device, and measuring acoustic vibrations at least one of emitted and absorbed inside the timepiece to obtain an electrical signal representative of the measured acoustic vibrations (acoustic signal). A magnitude of the electrical signal represents magnitude information of the measured acoustic vibrations as a function of time. The method further includes comparing the magnitude information with at least one reference magnitude information, and determining an authenticity of said timepiece based on the comparing.

In further embodiments of the invention, the at least one external excitation generates at least one acoustic vibration inside the timepiece.

In additional embodiments of the invention, the external device comprises at least one of a transducer and a striking element.

In embodiments, the transducer comprises at least one of a piezoelectric device and a tuning fork.

In additional embodiments, the striking element comprises at least one of a clapper and a striker.

In yet further embodiments of the invention, the external at least one excitation comprises at least one of regular vibrations, sequential vibrations, time-varied vibrations, intensity-varied vibrations, pulsed vibrations, and continuous vibrations with discontinuous frequencies.

In further embodiments of the invention, the measuring of the acoustic vibrations emitted inside the timepiece to obtain the electrical signal comprises converting the acoustic vibration captured by a microphone.

In additional embodiments of the invention, the method further comprises storing the electrical signal in a database as a reference signal.

In yet further embodiments of the invention, the method further comprises processing the electrical signal by a mathematical algorithm to convert the electrical signal to a frequency or time-frequency domain.

In further embodiments of the invention, the mathematical algorithm is selected from one of a Fourier transformation, a short-time Fourier transform, a Gabor transform, a Wigner transform, and a wavelet transform.

In additional embodiments of the invention, the measuring of the acoustic vibrations emitted inside the timepiece occurs when the timepiece is not running.

In yet further embodiments of the invention, the measuring of the acoustic vibrations emitted inside the timepiece occurs when the timepiece is running.

In further embodiments of the invention, the applying at least one external excitation is synchronous with a tic/tock noise emanated by the running timepiece.

In additional embodiments of the invention, the measuring of the acoustic vibrations emitted inside the timepiece occurs when at least one of a tic movement and a tock movement of the timepiece occurs.

In yet further embodiments of the invention, the measuring of the acoustic vibrations emitted inside the timepiece occurs between occurrences of a tic movement and a tock movement of the timepiece.

In further embodiments of the invention, the at least one external excitation comprises acoustic vibrations.

In additional embodiments of the invention, the acoustic vibrations comprise at least one of a single tone, two or more tones, a sweep, a white noise, a colored noise, a random or pseudo-random sequence, one impulse, and a sequence of two or more impulses.

In yet further embodiments of the invention; the at least one external excitation is continuous.

In further embodiments of the invention, the at least one external excitation is pulsed.

In yet further embodiments, the pulses are identical copies of one another.

In further embodiments, the pulses are different from one another.

In additional embodiments of the invention, the measuring of the acoustic vibrations emitted inside the timepiece at least partially overlaps in time with the at least one external excitation.

In yet further embodiments of the invention, the measuring of the acoustic vibrations emitted inside the timepiece does not overlap in time with the external excitation.

In further embodiments of the invention, the method further comprises measuring at least one background vibration when no external excitation is applied, and subtracting the at least one background vibration from the measured acoustic vibrations.

In additional embodiments of the invention, the at least one reference magnitude information comprises at least one of previously recorded data and a model.

In yet further embodiments of the invention, the model comprises data expected based on previous observations of one or more timepieces similar to the timepiece.

In further embodiments of the invention, the method further comprises issuing a signal indicating one of authenticity of the timepiece and non-authenticity of the timepiece.

In additional embodiments of the invention, the signal comprises at least one of: an alert, a hold signal, an alarm, and a notification.

In further embodiments of the invention, the method further comprises applying a specific excitation frequency to excite a resonator within the timepiece to extract a unique identifier for the timepiece.

An embodiment of the invention provides a system for authenticating a timepiece. The system includes an exciter for applying at least one external excitation to said timepiece using an external device, and a detector for measuring acoustic vibrations emitted inside the timepiece to obtain an electrical signal representative of the measured acoustic vibrations. The electrical signal indicates magnitude information comprising a variation of a magnitude of the measured acoustic vibrations as a function of time. The system further includes a comparator for comparing the magnitude information with at least one reference magnitude information, and an authenticator for determining an authenticity of said timepiece based on the comparing.

A further embodiment of the invention provides a method for creating an identifier for a timepiece. The method comprises applying at least one external excitation to the timepiece using an external device, measuring acoustic vibrations emitted inside the timepiece to obtain an electrical signal representative of the measured acoustic vibrations, and creating an identification code based on the electrical signal using a processor of a computing device.

BRIEF DESCRIPTION OF THE FIGURES

For a more complete understanding of the invention, as well as other objects and further features thereof, reference may be had to the following detailed description of the invention in conjunction with the following exemplary and non-limiting drawings wherein.

Figure 1:
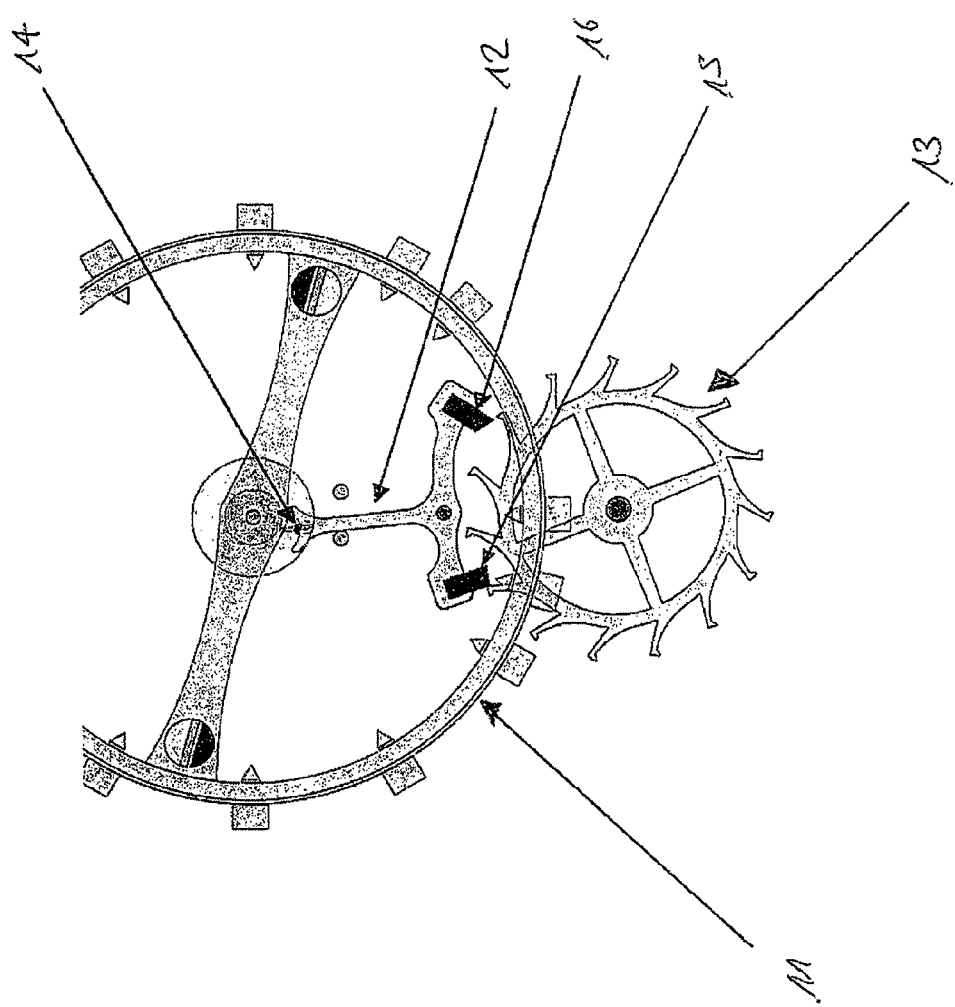
FIG. 1 is a schematic representation of an escapement in a timepiece.

Reference numbers refer to the same or equivalent parts of the present invention throughout the various figures of the drawings.

DETAILED DESCRIPTION OF EMBODIMENTS OF THE INVENTION

In the following description, the various embodiments of the present invention will be described with respect to the enclosed drawings.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description is taken with the drawings making apparent to those skilled in the art how the forms of the present invention may be embodied in practice.

As used herein, the singular forms "a," "an," and "the" include the plural reference unless the context clearly dictates otherwise.

The term acoustic should be intended encompass the sonic, sub-sonic and ultrasonic range, unless otherwise specified.

Except where otherwise indicated, all numbers expressing physical quantities, such as frequency, time, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by the present invention. At the very least, and not to be considered as an attempt to limit the application of the doctrine of equivalents to the scope of the claims, each numerical parameter should be construed in light of the number of significant digits and ordinary rounding conventions.

Additionally, the recitation of numerical ranges within this specification is considered to be a disclosure of all numerical values and ranges within that range. For example, if a range is from about 1 to about 50, it is deemed to include, for example, 1, 7, 34, 46.1, 23.7, or any other value or range within the range.

The various embodiments disclosed herein can be used separately and in various combinations unless specifically stated to the contrary.

Embodiments of the present invention relates to a method and system for authenticating an object or device using external excitation. In embodiments, the object or device may comprise a timepiece (e.g., a watch). In additional embodiments, the object or device may comprise mobile telephones or mechanical spare parts. Also suitable are any objects having small mechanical resonators that are purposefully inserted, and that do not alter the object's functionality.

A timepiece, such as a watch, may comprise a mechanical movement which produces a characteristic noise, which is commonly referred to as tick-tock. This tick-tock sound is due to the impacts occurring between the various mechanical parts of the escapement of the timepiece. The escapement is a device for transferring energy to the time-keeping element (the so-called impulse action), and for allowing the number of its oscillations to be counted (the locking action). The ticking sound is the sound of the gear train stopping at the escapement locks.

FIG. 1 shows a representation of the main parts of an escapement. An escapement comprises a balance wheel 11, a pallet fork 12 and an escapement wheel 13. The balance wheel 11 comprises an impulse pin 14, which strikes against the pallet fork 12. Further, the escapement wheel 13 comprises teeth that are arranged to strike an entry pallet jewel 15 and an exit pallet jewel 16 of the pallet fork 12.

While mechanical shocks within the timepiece may be a source of vibrations, which can be recorded and used for authentication/identification purposes, the present invention utilizes an external source of excitation, as this can be advantageous in several circumstances. For example, a timepiece may not be operating (e.g., broken), such that there are no generated internal vibrations from the operation of the movement (e.g., no "tic-tock" sound). With embodiments of the present invention, an external source of excitation is utilized to generate internal vibrations in the timepiece, which may be used to identify and/or authenticate the timepiece. That is, in accordance with aspects of the invention, the external vibration generates at least one acoustic vibration inside the timepiece, which may be used to identify and/or authenticate a timepiece. Additionally, in accordance with additional features of embodiments of the invention, the transmission of sound inside the timepiece may further give information on the nature of the material (e.g., material type, such as, lead, steel, etc.).

Using an external source of excitation may be advantageous even with a working timepiece, as some of the parts whose vibrations can give rise to a characteristic signal may be only weakly excited by the internal shocks. In particular, even if a timepiece is working, the sound generated by internal excitation is mostly localized in a specific region of the timepiece (e.g., in the movement, at the balance wheel/escapement assembly). As such, with the internally generated vibrations (e.g., the tic-tock sounds), an acoustic signature may only be based (or mostly based) on the specific region of the timepiece (e.g., in the movement). With embodiments of the present invention, however, by using an external excitation (e.g., vibration), additional information about the timepiece (e.g., other vibrational frequencies) may be determined, and used for identification and/or authentication. Additionally, by utilizing an external excitation, the excitation can be tailored with substantial freedom (in contrast to an internal excitation due to the movement, where the excitation is given by the characteristics of the movement). For example, in embodiments, the frequency spectrum of the excitation, the amplitude of the excitation and/or the time-profile of the excitation may be controlled.

In embodiments, the acoustic vibration can advantageously serve as a basis for material and/or structural analysis of said timepiece. For example, the acoustic vibration may differ between different materials, such that an analysis of the acoustic signal may be used to identify the material of the timepiece.

In further embodiments, rather than one microphone and/or excitation source to extract said acoustic vibration, a plurality of devices (e.g., microphones and/or excitation sources) may be used, to show and reveal different paths of propagation of the vibration inside the timepiece (and the associated delays), reflecting the structure and/or material composition of the timepiece. With one exemplary and non-limiting embodiment, three microphones may be used to localize the source of vibration inside a timepiece.

According to an embodiment of a method for authenticating a timepiece according to the invention, an external source of excitation is applied to a timepiece to be authenticated, and the acoustic vibrations of the timepiece are measured, for example, using a microphone, such as a contact piezoelectric microphone. The acoustic vibrations emitted by the timepiece are measured and an electrical signal is obtained, which indicates a variation of the magnitude of the measured acoustic vibrations as a function of time.

Figure 2:
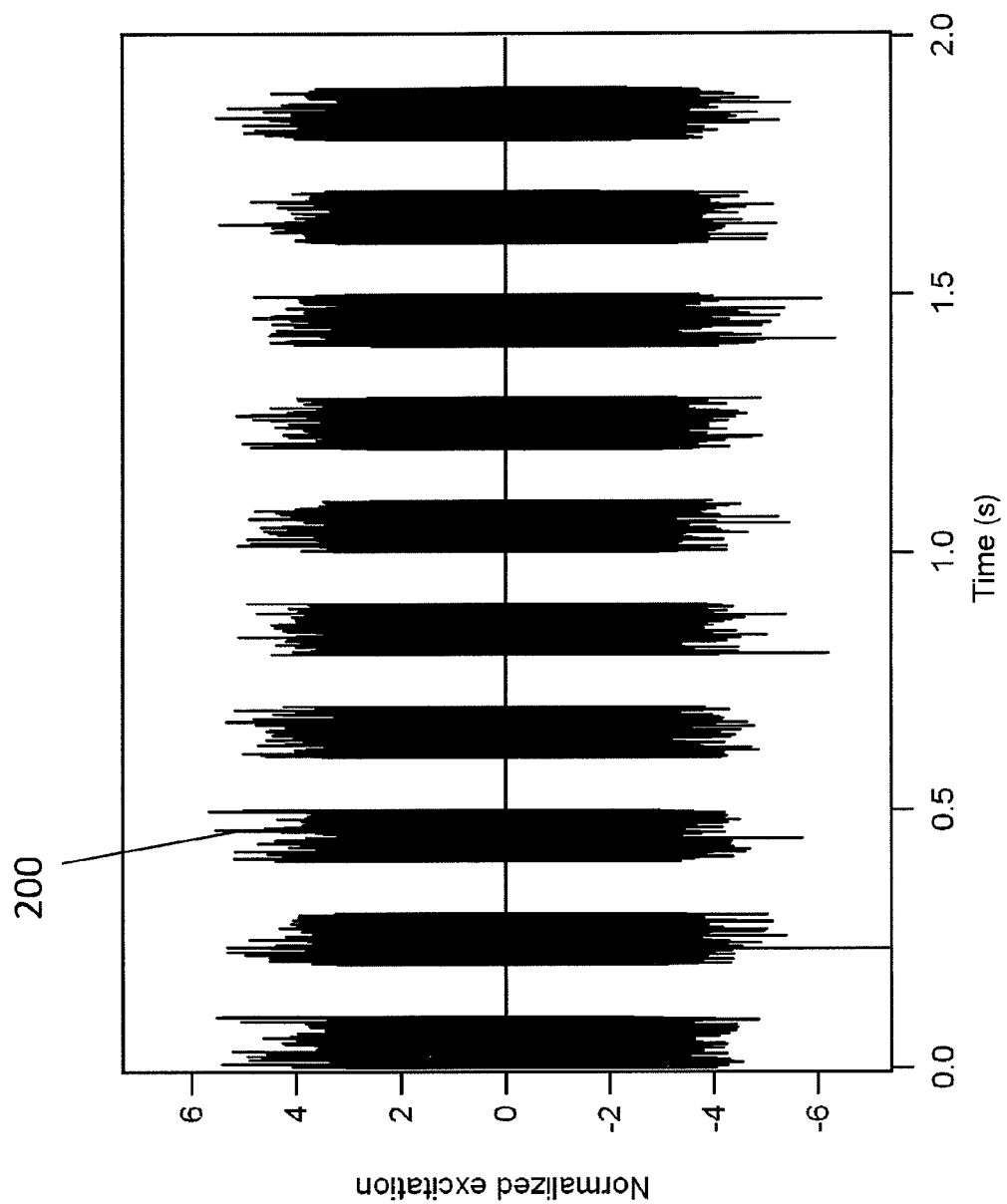
FIG. 2 shows an exemplary excitation signal in accordance with embodiments of the invention.

FIG. 2 shows an exemplary excitation signal 200 on a non-working timepiece in accordance with embodiments of the invention. As shown in FIG. 2, the exemplary excitation signal 200 is depicted as a normalized excitation signal versus time. In embodiments, the external excitation signal 200 may be generated using an external device. In embodiments of the invention, the external device may include at least one of a transducer (e.g., a piezoelectric device or a tuning fork), and a striking element (e.g., a clapper or a striker) amongst other contemplated external devices. It should also be noted that in some embodiments, the external excitation may not require a transducer, for example, in the case of an electro-magnetic excitation.

In embodiments, the two functions of excitation and detection could be coupled in a single transducer that is operable to produce the excitation and detect the acoustic signal.

As shown with the exemplary excitation signal of FIG. 2, the excitation signal 200 may include a regular sequence of excitation regions spaced apart (e.g., 100 ms on, 100 ms off, 100 ms on, 100 ms off, etc.) by regions of non-excitation. With such an exemplary excitation signal 200, the internal vibrations may be detected during the periods of non-excitation. That is, in embodiments, the measuring of the acoustic vibrations emitted inside the timepiece does not overlap in time with the external excitation. Additionally, the internal vibrations may be detected during the periods overlapping (e.g., partially or totally with) the periods of excitation. That is, in embodiments, the measuring of the acoustic vibrations emitted inside the timepiece may at least partially overlap in time with the at least one external vibration.

With other contemplated embodiments, the external excitation signal may comprise one or more of sequential vibrations, time-varied vibrations, intensity-varied vibrations, pulsed vibrations, acoustic vibrations, and a non-stop (or continuous) vibration with discontinuous frequencies, continuous vibration with a continuous frequency. In embodiments of the invention, the acoustic vibrations may comprise at least one of a single tone, two or more tones, a sweep, a white noise, a colored noise, a random or pseudo-random sequence, one impulse, and a sequence of two or more impulses.

Figure 3:
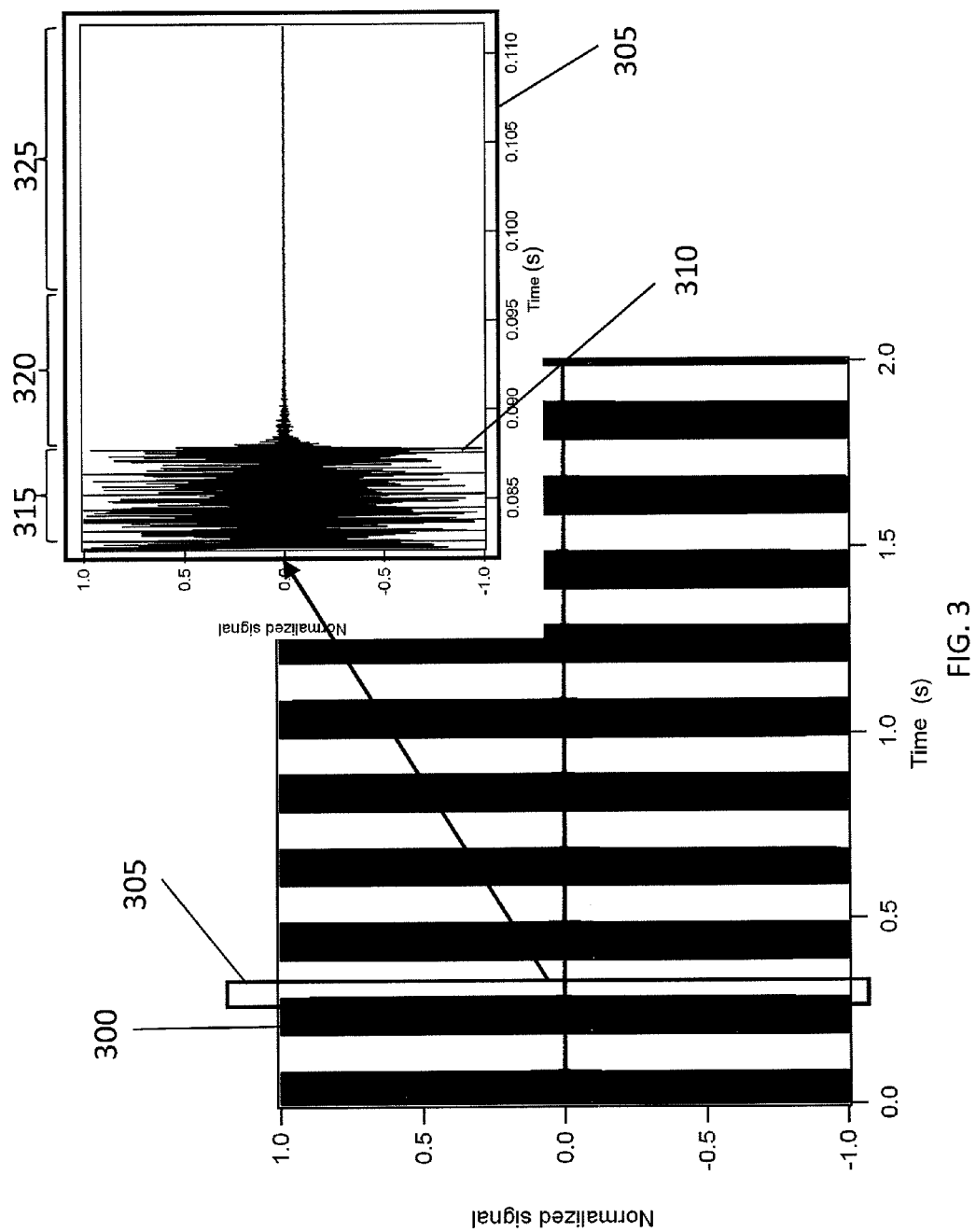
FIG. 3 shows an exemplary detected signal in accordance with embodiments of the invention.

FIG. 3 shows an exemplary detected signal 300 in accordance with embodiments of the invention. As shown in FIG. 3, a section (depicted within box 305) of the exemplary detected signal 300 is enlarged to illustrate a portion 310 of the exemplary detected signal 300. As is shown in FIG. 3, the portion 310 of the exemplary detected signal 300 generally includes three zones (315, 320, and 325). In accordance with embodiments of the invention, zone 315 of the exemplary detected signal 300 may include a detection of the external excitation signal and a detection of the internal vibrations emitted by the timepiece due to application of the external excitation signal. Zone 320 of the exemplary detected signal 300 includes a detection of the internal vibrations emitted by the timepiece that are attributable to the applied external excitation. Zone 325 of the exemplary detected signal 300 includes a detection of the background noise (e.g., such as acoustic and electrical noise picked-up by the microphone).

Figure 4:
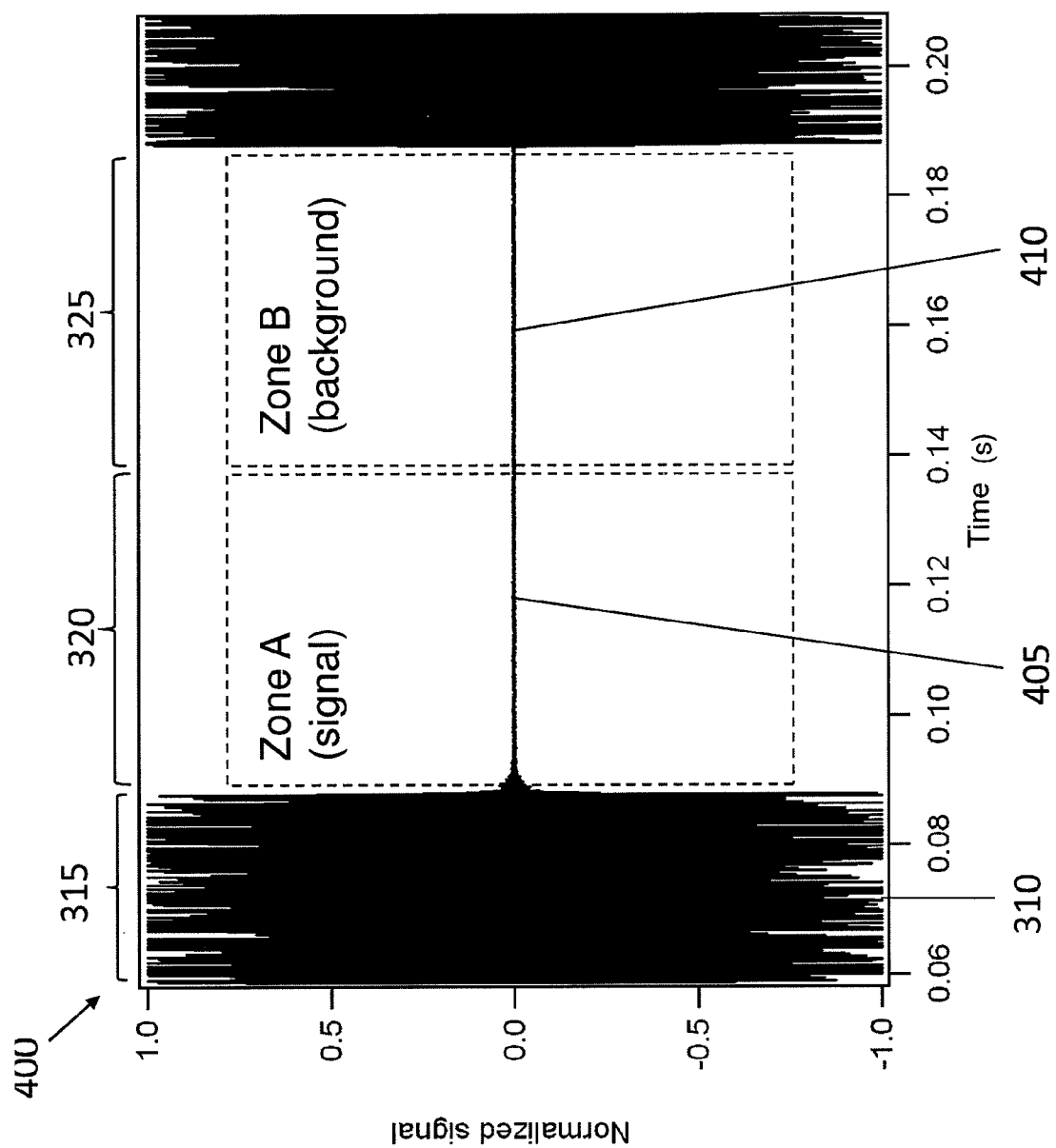
FIG. 4 shows an exemplary background subtraction signal in accordance with embodiments of the invention.

FIG. 4 shows an exemplary detected signal 400 with an identification of a background subtraction signal in accordance with embodiments of the invention. As shown in FIG. 4, the exemplary detected signal may be divided into three zones (315, 320, and 325). As noted above, zone 315 of the exemplary detected signal 400 may include a detection of the external excitation signal and a detection of the internal vibrations emitted by the timepiece due to application of the external excitation signal. Zone 315 may include both a detection of the external excitation signal and a detection of the internal vibrations emitted by the timepiece due to application of the external excitation signal. This portion of the detected signal 400 may be less suitable for identification and/or authentication purposes, as its dominant contribution comes from direct transmission of the external excitation without excitation of internal vibrations. Zone 320 (also designated as Zone A) of the exemplary detected signal 400 includes a detection of the internal vibrations 405 emitted by the timepiece that are attributable to the applied external excitation. Because these vibrations persist for a time after the excitation has been turned off, they contribute substantially to the signal in zone 320. In zone 325 (also designated as Zone B) of the exemplary detected signal 400, the vibrations have substantially or completely decayed. Hence, a comparison between the signal measured in zone 320 and the signal measured in zone 325 conveniently allows to discriminate between useful signal (coming from vibrations emitted by the timepiece as a result of the external excitation) and background noise, which is not attributable to the applied external excitation (such as, for example, acoustical ambient noise, building vibrations, etc.).

In accordance with embodiments of the invention, the acoustic vibrations emitted by a timepiece to be authenticated are measured and an electrical signal is obtained, which indicates a variation of a magnitude of the measured acoustic vibrations as a function of time. This electrical signal may be transformed into a frequency domain, so as to obtain a frequency-domain power spectrum indicating a variation of a power of the electrical signal as a function of frequency. The frequency-domain transform to be used according to an exemplary embodiment may be one of the usual frequency-domain transforms, such as a Fourier transform, in particular a Fast Fourier transform. The frequency-power spectrum of the measured acoustic vibrations of the timepiece to be authenticated reveals several peaks in the power spectrum representation at several frequencies.

This frequency information may be extracted from the frequency-domain power spectrum and compared with reference frequency information, which has been previously stored for the timepiece model. This comparison enables derivation of information making it possible to authenticate a timepiece by simply comparing the frequency information obtained for the timepiece to be authenticated with the reference frequency information for the timepiece model to be authenticated.

In embodiments, a time-frequency representation may be used to provide information on which frequencies are present at which time. A time-frequency representation can therefore be used to associate specific frequencies with specific events taking place in the time domain. For example, a time-frequency representation can be used to determine the lifetime of the vibration associated with a given resonant frequency.

According to embodiments of the present invention, a time-frequency transform to be used may be one among the several time-frequency transforms available and known to the person skilled in the art. In particular, only to cite a few possible exemplary transforms, the transform into a time-frequency representation may be one of the short-time Fourier transform, a Gabor transform, a Wigner transform, and a wavelet transform.

A wavelet transform is described, for example, in C. Torrence and G. P. Compo, *Bulletin of the American Meteorological Society*, 79, 1998. The use of a wavelet transform represents an exemplary embodiment of the present invention, since the wavelet transform is a convenient tool for time-frequency analysis, with a number of interesting features, such as the possibility to adapt the time-frequency resolution to the problem under investigation, as well as the good mathematical properties. The continuous wavelet transform takes a time-domain signal s(t), the electrical signal of the measured acoustic vibrations emitted by the timepiece to be authenticated, the electrical signal indicating a variation of the magnitude of the measured acoustic vibrations as a function of time, and transforms this time-domain signal into a time-frequency representation W(f, t), which is defined by the following equation (1):

$$W(f, t) = \sqrt{\frac{2\pi f}{c}} \int_{-\infty}^{\infty} s(t') \psi^* \left( \frac{2\pi f(t' - t)}{c} \right) dt' \qquad (1)$$

where:
ψ is the wavelet function (there are several types to choose from); and
c is a constant, which depends on the chosen wavelet function.

With additional embodiments, a time-frequency representation may be obtained using a Morlet wavelet (2):

$$\psi_\omega(x) = \pi^{-1/4} \exp(i\omega x - x^2/2) \qquad (2)$$

with: ω=40 and $$c = \frac{\omega + \sqrt{2 + \omega^2}}{2} \approx 40.01$$

By using this time-frequency information, which is obtained from a time-frequency representation of the electrical signal obtained by measuring acoustic vibrations emitted by the timepiece to be authenticated, information on an authenticity of the timepiece can be derived. In order to do so, the time-frequency information is extracted from the time-frequency representation and compared with reference time-frequency information, which has been previously stored for the timepiece model. By comparing the time-frequency information extracted for the timepiece to be authenticated with the reference time-information for the timepiece model, the authenticity (or lack thereof) of the timepiece can be derived.

In further embodiments of the invention, the method further comprises measuring at least one background vibration when no external vibration is applied, and subtracting the at least one background vibration from the measured acoustic vibrations.

Figure 5:
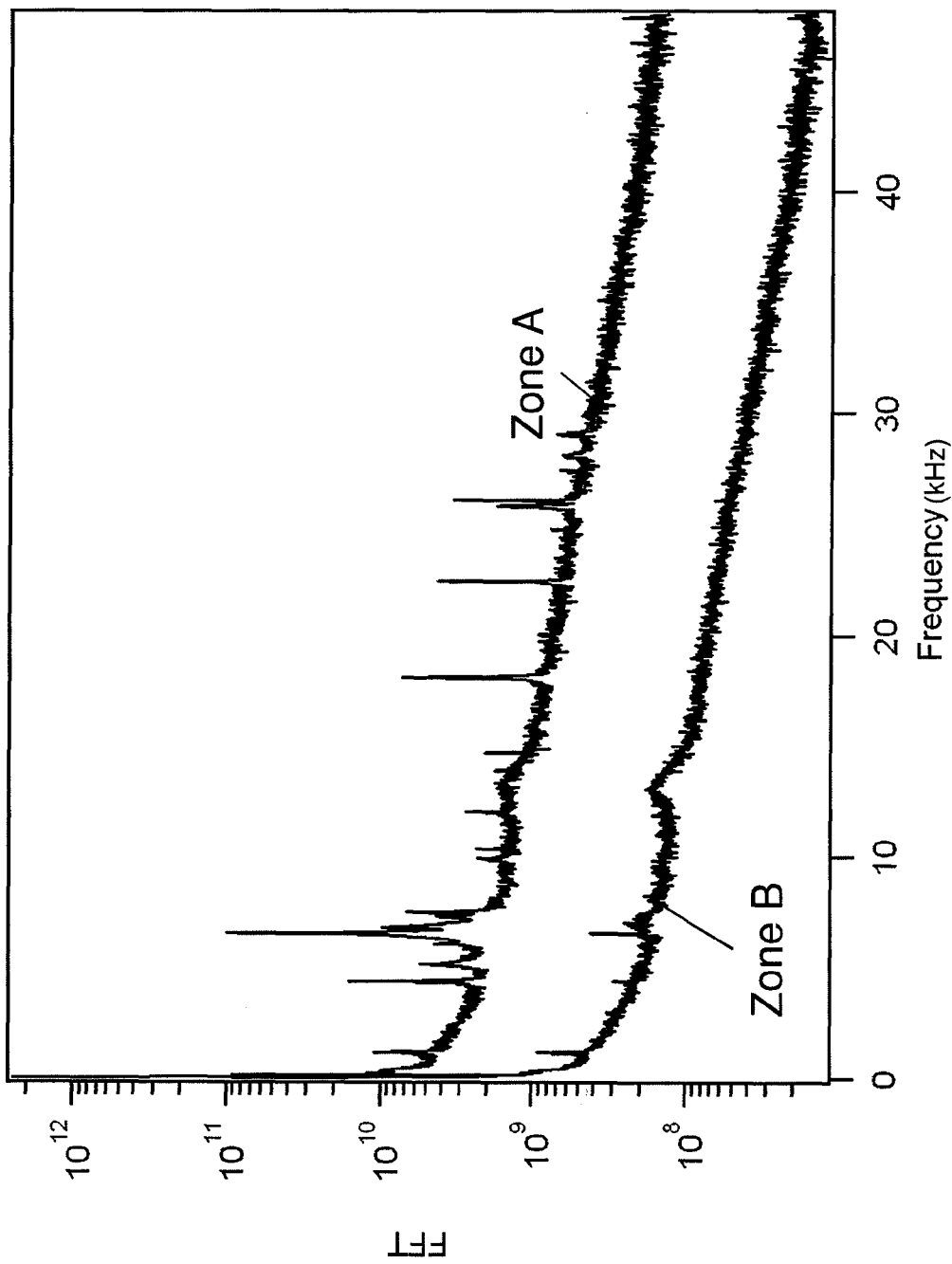
FIG. 5 shows an exemplary signal/background Fourier transform for the purpose of background subtraction in accordance with embodiments of the invention.

FIG. 5 shows an exemplary signal/background Fourier transform for the purpose of background subtraction in accordance with embodiments of the invention. More specifically, FIG. 5 shows an exemplary Fourier transform of the Zone A portion of the signal and the Zone B portion of the signal in accordance with embodiments of the invention. In embodiments of the invention, a background subtraction may be performed (e.g. by taking the ratio of the two Fourier Transforms) to subtract the background noise (e.g., as detected in Zone B) from the detected signal (e.g., as detected in Zone A) to arrive at an identification/authentication signal (i.e., representative of the internal vibrations of the timepiece that are attributable to the applied external excitation).

Figure 6:
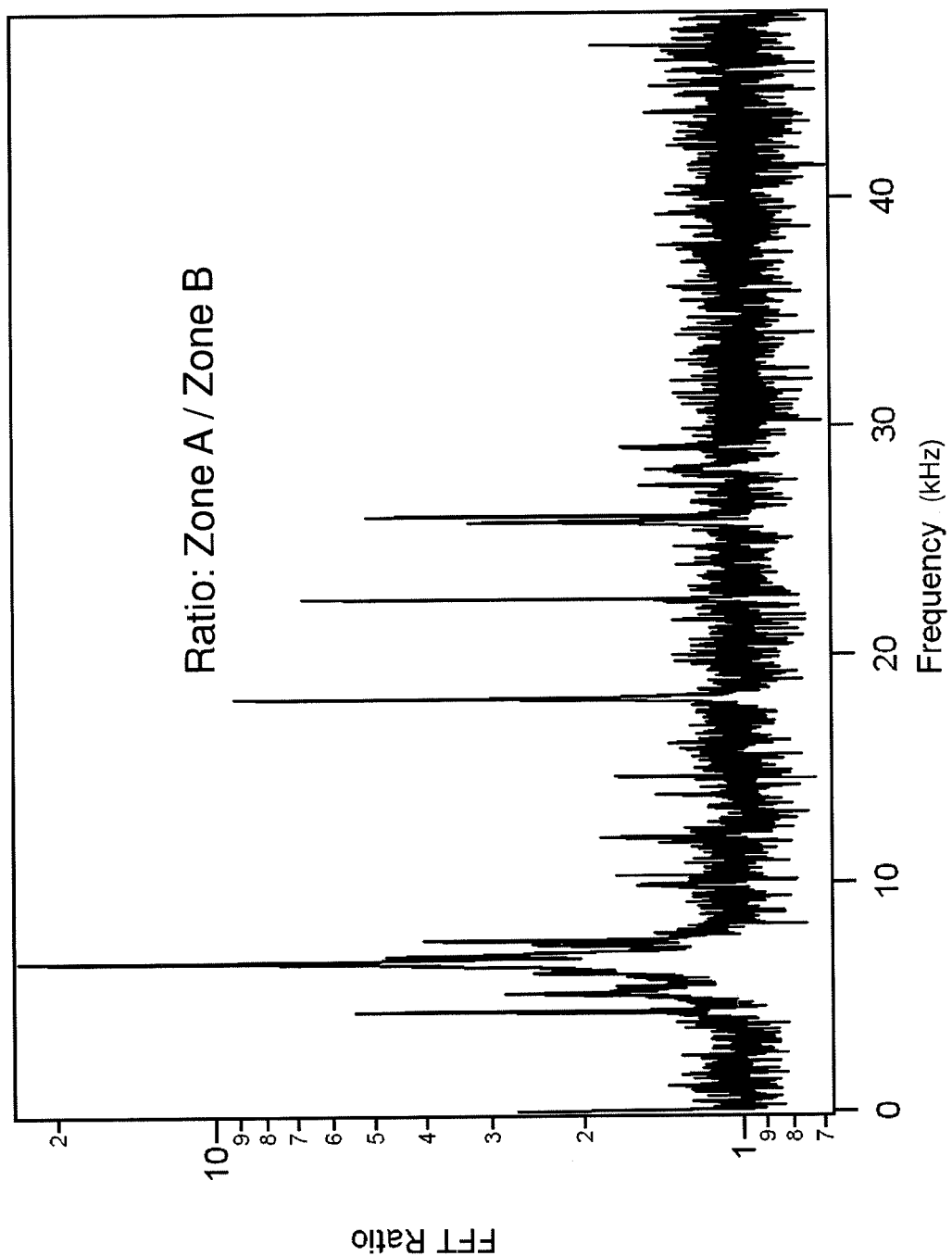
FIG. 6 shows an exemplary background subtraction ratio Fourier transform in accordance with embodiments of the invention.

FIG. 6 shows an exemplary background subtraction ratio Fourier transform in accordance with embodiments of the invention. More specifically, FIG. 6 shows an exemplary Fourier transform ratio of the Zone A portion of the signal to the Zone B portion of the signal in accordance with embodiments of the invention. In embodiments of the invention, the ratio of the detected signal (e.g., as detected in Zone A) to the background noise (e.g., as detected in Zone B) may be used as an identification/authentication signal (i.e., representative of the internal vibrations of the timepiece that are attributable to the applied external excitation).

In accordance with embodiments of the invention, the extracted information (e.g., the signal resulting from background subtraction and/or the ratio signal) may then be compared with reference information. This reference information has been previously measured and stored for the timepiece model that is to be authenticated. By comparing the extracted information obtained for the timepiece to be authenticated with the reference information, information regarding an authenticity of the timepiece to be authenticated can be derived.

According to an embodiment of the present invention, information on the width of the spectral peak can also be used for authentication and/or identification purposes.

It has been observed by the inventors of the embodiments of the present invention that the reliability and degree of precision of the embodiments of the invention are such that it is possible to even identify differences between the timepieces of an identical model. Indeed, because of manufacturing tolerances, even two timepieces of an identical model differ from each other. When applying the principles underlined in the present invention to different timepieces from the same series and the same manufacturer, it can be seen that the corresponding acoustic measurements are different and the extracted relevant respective pieces of frequency information, which characterize the fingerprint of the respective timepiece, are different. Hence, an identifier (e.g., a unique identifier) can be defined for a timepiece without having to open the timepiece.

The above-described measurements of a particular timepiece should not change over time (i.e., remain stable). For example, as long as components of the watch are not touched or manipulated, the above-described measurements of a particular timepiece will not change. Of course, with maintenance of the timepiece (e.g., when the timepiece is opened), the above-described measurements may be affected. As such, when timepiece maintenance is performed (e.g., when the timepiece is opened), the timepiece should be recertified (e.g., the acoustic signature of the timepiece should be recaptured, and the results of the one or more the above-described measurements should be identified and stored). In embodiments, once the timepiece is recertified, the results of the one or more of said above-described measurements may also be linked with the timepiece ID (e.g., the timepiece serial number), for example, in a database.

While the above-described measurements of a timepiece should not change over time, the embodiments of the invention contemplate that some of the above-described measurements of respective timepiece may change (e.g., slightly) over time. Thus, in accordance with embodiments of the invention, a threshold for determining a positive authentication of a timepiece may be configured (e.g., lowered) in dependence upon an age of the timepiece. That is, in embodiments, an older timepiece may be subjected to a lower threshold for a positive authentication via comparison with stored time measurements, frequency measurements, and/or magnitude measurements (or stored identifiers based upon the measurements). In embodiments, the timepiece may be recertified on a regular basis (e.g., yearly) to account for the evolution (e.g., any property changes) of the timepiece over time.

With further contemplated embodiments, the analysis of a timepiece may be in two levels (e.g., a less intense first level and a more intense second level). For example, with a first level of analysis (e.g., an initial assessment), the timepiece may be identified by a make and model (e.g., using a peak within a range of frequencies), to determine if the timepiece is authentic (i.e., verified as a particular make and model). With this first level of analysis, an assessment may determine, for example, that the timepiece is in fact a particular make and/or model. A second level of analysis may include a deeper analysis of the emitted sounds, to identify a unique "finger print" for the timepiece (e.g., using a specific peak or a peak within a range of frequencies). This unique "finger print" may be stored in a database and/or compared with previously stored finger prints to positively identify the timepiece. In embodiments, either or both of the first and second levels of analysis may be done with a new timepiece, or with used timepieces that have not been previously analyzed.

While above embodiments have been described with regard to a timepiece that is not working or "running" (e.g., is broken or unwound), with further contemplated embodiments, the measuring of the acoustic vibrations emitted within the timepiece may be performed while the timepiece is running. With such an embodiment, the applying at least one external vibration may be synchronous with a tic/tock noise emanated by the timepiece. In additional embodiments of the invention, the measuring of the acoustic vibrations emitted inside the timepiece may be performed when at least one of a tic movement and a tock movement of the timepiece occurs. In yet further embodiments of the invention, the measuring of the acoustic vibrations emitted inside the timepiece may be performed between occurrences of a tic movement and a tock movement of the timepiece.

With further contemplated embodiments, more than one bit of information may be extracted from the timepiece, with additional (or specific) stimulation (or excitation). For example, a timepiece may be configured, such that a unique ID may be extracted using a specific frequency of excitation. For example, the timepiece may be provided with a resonator, which is excited by a specific frequency, to create a unique ID.

Figure 7:
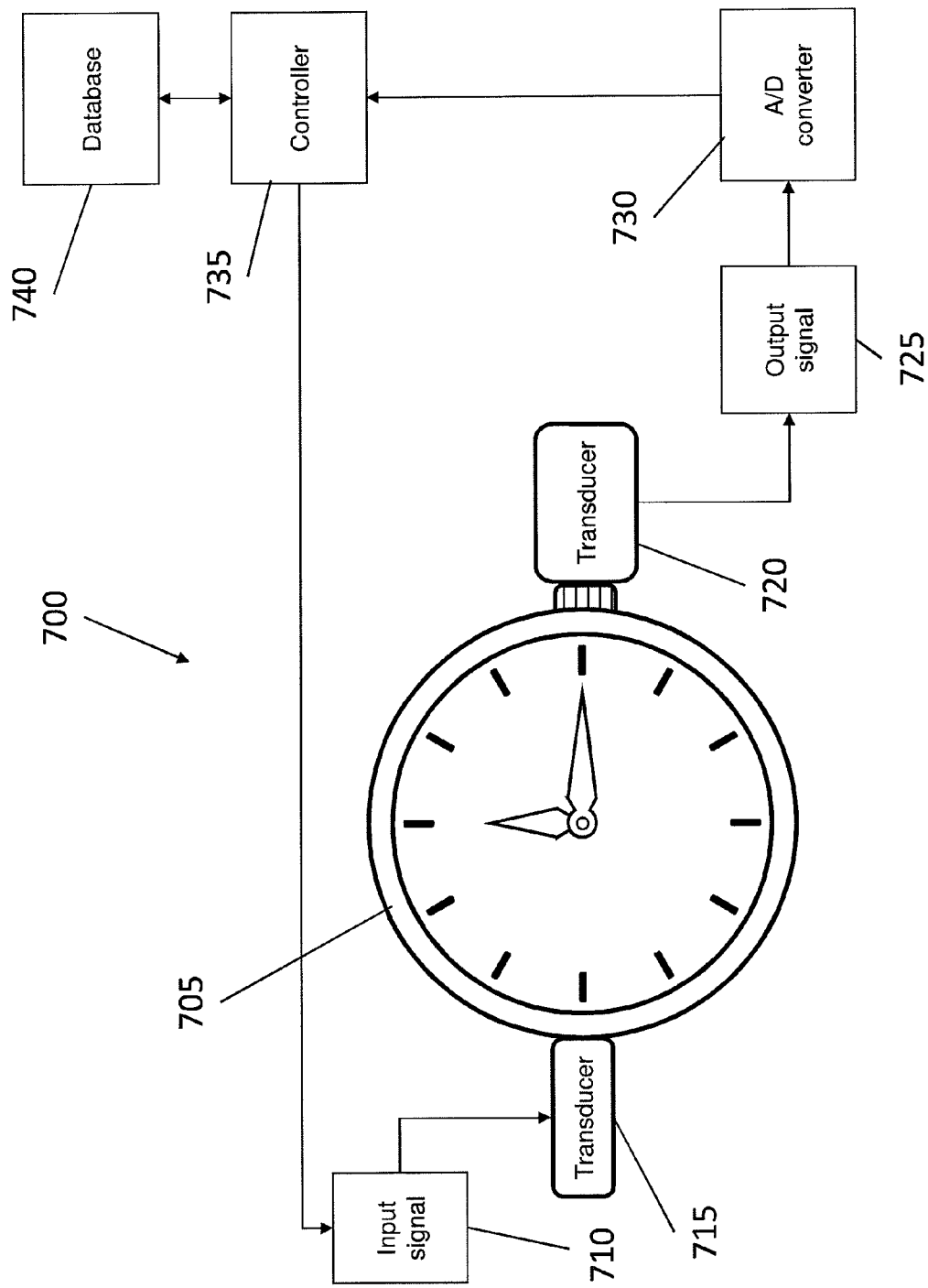
FIG. 7 shows an exemplary signal detection system in accordance with embodiments of the invention.

FIG. 7 shows an exemplary and non-limiting signal detection system 700 in accordance with embodiments of the invention. As shown in FIG. 7, the exemplary signal detection system 700 includes an input signal generation tool 710 operable to generate an input signal. The generated input signal is sent to an external excitation device 715 (e.g., a transducer). The exemplary and non-limiting signal detection system 700 illustrates a transducer as the external excitation device 715, which in embodiments of the invention, may be a piezoelectric device and/or a tuning fork, amongst other contemplated external excitation devices. In other embodiments, the external excitation device may be a (small) striking element, such as a clapper or a striker. The generated input signal may be configured to produce (via the external excitation device) one or more of regular vibrations (e.g., of approximately constant amplitude and spectrum), sequential vibrations, time-varied vibrations, intensity-varied vibrations, pulsed vibrations, and continuous (e.g., non-stop) vibrations having discontinuous frequencies.

As further shown in FIG. 7, the external vibration device 715 (e.g., a transducer) is placed in proximity to (e.g., in physical contact with) a timepiece 705. A detection device 720 (e.g., a transducer) is placed in contact with the timepiece 705 to detect the vibrations emitted by the timepiece 705. In embodiments, the detection device may comprise a transducer, such as, a microphone, amongst other contemplated detection devices.

In accordance with embodiments of the invention, the detection device 720 detects an output signal 725. The output signal 725 is sent to an analog/digital converter 730, which is operable to convert the analog output signal into a digital signal. The digital output signal is sent to a controller 735. In embodiments, the controller 735 is operable to process the digital signal (e.g., using a Fast Fourier transform). Further, the controller 735 is operable to further process the signal (e.g., using a subtraction of the background signal from the detected signal and/or a ratio of the detected signal to the background signal, as discussed above) to determine an identification/authentication signature for the timepiece. Additionally, the controller 735 is operable to store the identification/authentication signature for the timepiece in a storage device 740 (e.g., a database). Also, as shown in FIG. 7, the controller 735 is in communication with the input signal device 710, and is operable to control a generation of the input signal.

System Environment

As will be appreciated by one skilled in the art, the present invention may be embodied as a system, a method or a computer program product. Accordingly, the present invention may take the form of an entirely hardware embodiment, an entirely software (except for the transducers and A/D converters) embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer-usable program code tangibly embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium include the following:

an electrical connection having one or more wires,
a portable computer diskette,
a hard disk,
a random access memory (RAM),
a read-only memory (ROM),
an erasable programmable read-only memory (EPROM or Flash memory),
an optical fiber,
a portable compact disc read-only memory (CDROM),
an optical storage device,
a transmission media such as those supporting the Internet or an intranet,
a magnetic storage device,
a usb key,
a certificate,
a perforated card, and/or
a mobile phone.

In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network. This may include, for example, a local area network (LAN) or a wide area network (WAN), or the connection may be made to an external computer (for example, through the Internet using an Internet Service Provider). Additionally, in embodiments, the present invention may be embodied in a field programmable gate array (FPGA).

Figure 8:
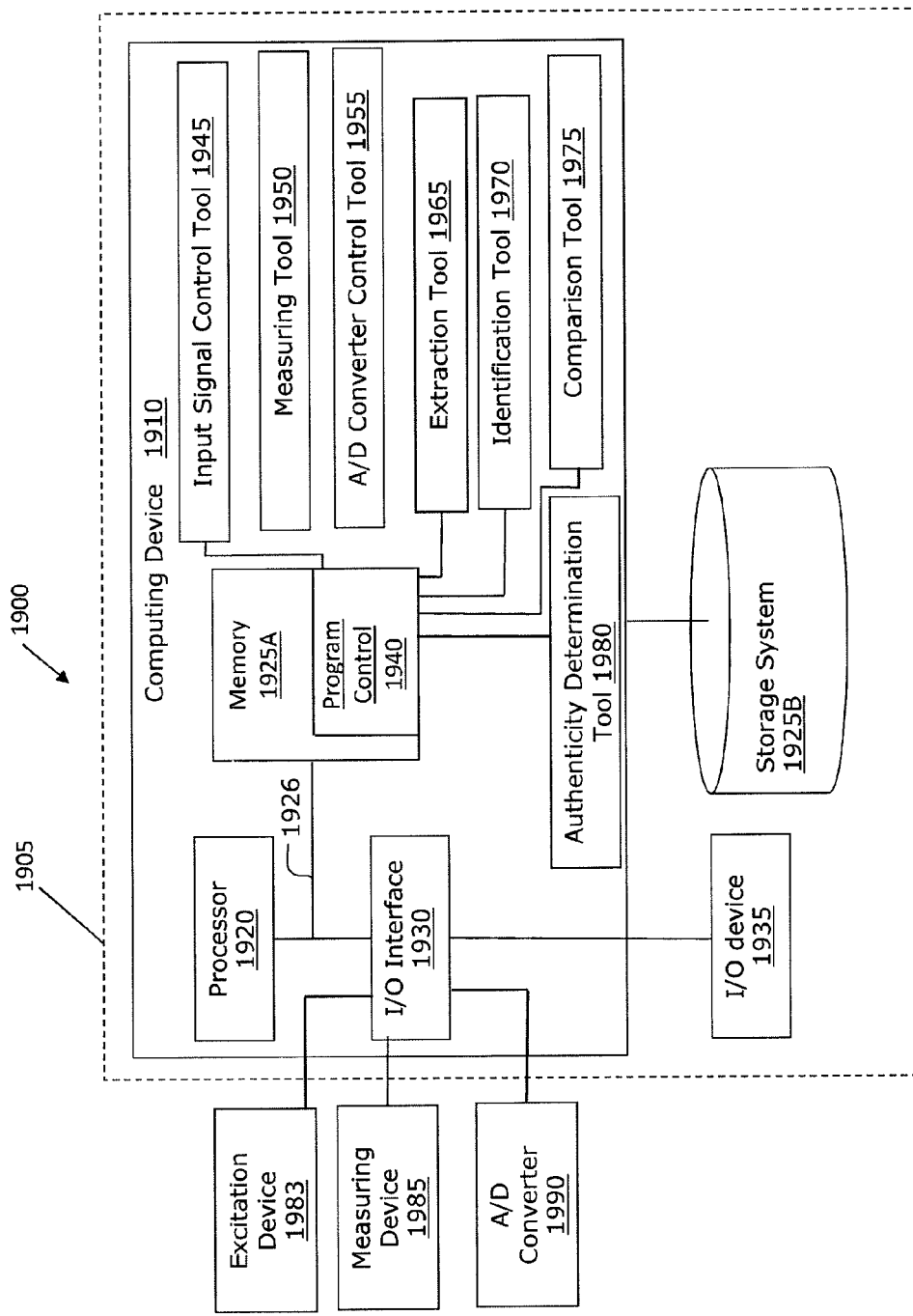
FIG. 8 shows an illustrative environment for managing the processes in accordance with embodiments of the invention.

FIG. 8 shows an illustrative environment 1900 for managing the processes in accordance with the invention. To this extent, the environment 1900 includes a server or other computing system 1905 that can perform the processes described herein. In particular, the server 1905 includes a computing device 1910. The computing device 1910 can be resident on a network infrastructure or computing device of a third party service provider (any of which is generally represented in FIG. 8). In embodiments of the present invention, the computing device 1910 may be used as the controller 735 depicted in FIG. 7.

In embodiments, the computing device 1910 includes an input signal control tool 1945, a measuring tool 1950, an analog/digital converter control tool 1955, an extraction tool 1965, an identification tool 1970, a comparison tool 1975, and an authenticity determination tool 1980, which are operable to create an external excitation, measure one or more detected sounds or vibrations, control an analog/digital converter, extract from an electrical signal or from a representation of said electrical signal in a time or time-frequency domain at least one of: magnitude information on a magnitude of the detected acoustic signal, time information of the detected acoustic signal, and frequency information of the detected acoustic signal, create an identifier based on the extracted information, compare the extracted information with stored information, and determine an authenticity, e.g., the processes described herein. The input signal control tool 1945, the measuring tool 1950, the analog/digital converter control tool 1955, the extraction tool 1965, the identification tool 1970, the comparison tool 1975, and the authenticity determination tool 1980 can be implemented as one or more program code in the program control 1940 stored in memory 1925A as separate or combined modules.

The computing device 1910 also includes a processor 1920, memory 1925A, an I/O interface 1930, and a bus 1926. The memory 1925A can include local memory employed during actual execution of program code, bulk storage, and cache memories which provide temporary storage of at least some program code in order to reduce the number of times code must be retrieved from bulk storage during execution. In addition, the computing device includes random access memory (RAM), a read-only memory (ROM), and an operating system (O/S).

The computing device 1910 is in communication with the external I/O device/resource 1935 and the storage system 1925B. For example, the I/O device 1935 can comprise any device that enables an individual to interact with the computing device 1910 or any device that enables the computing device 1910 to communicate with one or more other computing devices using any type of communications link. The external I/O device/resource 1935 may be for example, a handheld device, PDA, handset, keyboard, smartphone, etc. Additionally, in accordance with aspects of embodiments of the invention, the environment 1900 includes an excitation device (or exciter) 1983 for generating an external excitation, a measuring device (or measurer) 1985 for measuring sound vibrations (e.g., sonic emissions) from one or more timepieces, and an analog/digital converter 1990 for converting the detected analog signal into a digital signal.

In general, the processor 1920 executes computer program code (e.g., program control 1940), which can be stored in the memory 1925A and/or storage system 1925B. Moreover, in accordance with embodiments of the invention, the program control 1940 having program code controls the input signal control tool 1945, the measuring tool 1950, the analog/digital converter control tool 1955, the extraction tool 1965, the identification tool 1970, the comparison tool 1975, and the authenticity determination tool 1980. While executing the computer program code, the processor 1920 can read and/or write data to/from memory 1925A, storage system 1925B, and/or I/O interface 1930. The program code executes the processes of the invention. The bus 1926 provides a communications link between each of the components in the computing device 1910.

The computing device 1910 can comprise any general purpose computing article of manufacture capable of executing computer program code installed thereon (e.g., a personal computer, server, etc.). However, it is understood that the computing device 1910 is only representative of various possible equivalent computing devices that may perform the processes described herein. To this extent, in embodiments, the functionality provided by the computing device 1910 can be implemented by a computing article of manufacture that includes any combination of general and/or specific purpose hardware and/or computer program code. In each embodiment, the program code and hardware can be created using standard programming and engineering techniques, respectively.

Similarly, the computing infrastructure 1905 is only illustrative of various types of computer infrastructures for implementing the invention. For example, in embodiments, the server 1905 comprises two or more computing devices (e.g., a server cluster) that communicate over any type of communications link, such as a network, a shared memory, or the like, to perform the process described herein. Further, while performing the processes described herein, one or more computing devices on the server 1905 can communicate with one or more other computing devices external to the server 1905 using any type of communications link. The communications link can comprise any combination of wired and/or wireless links; any combination of one or more types of networks (e.g., the Internet, a wide area network, a local area network, a virtual private network, etc.); and/or utilize any combination of transmission techniques and protocols.

Flow Diagrams

Figure 9:
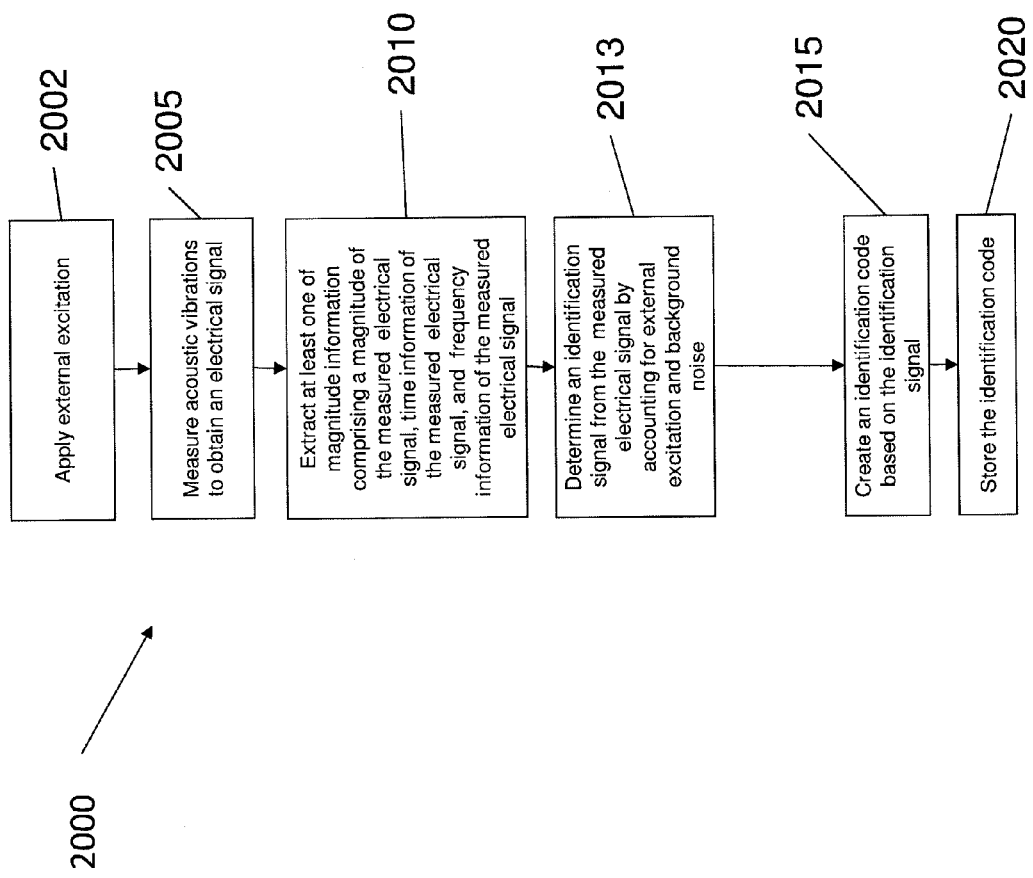
FIGS. 9 and 10 show exemplary flows for performing aspects of embodiments of the present invention.
Figure 10:
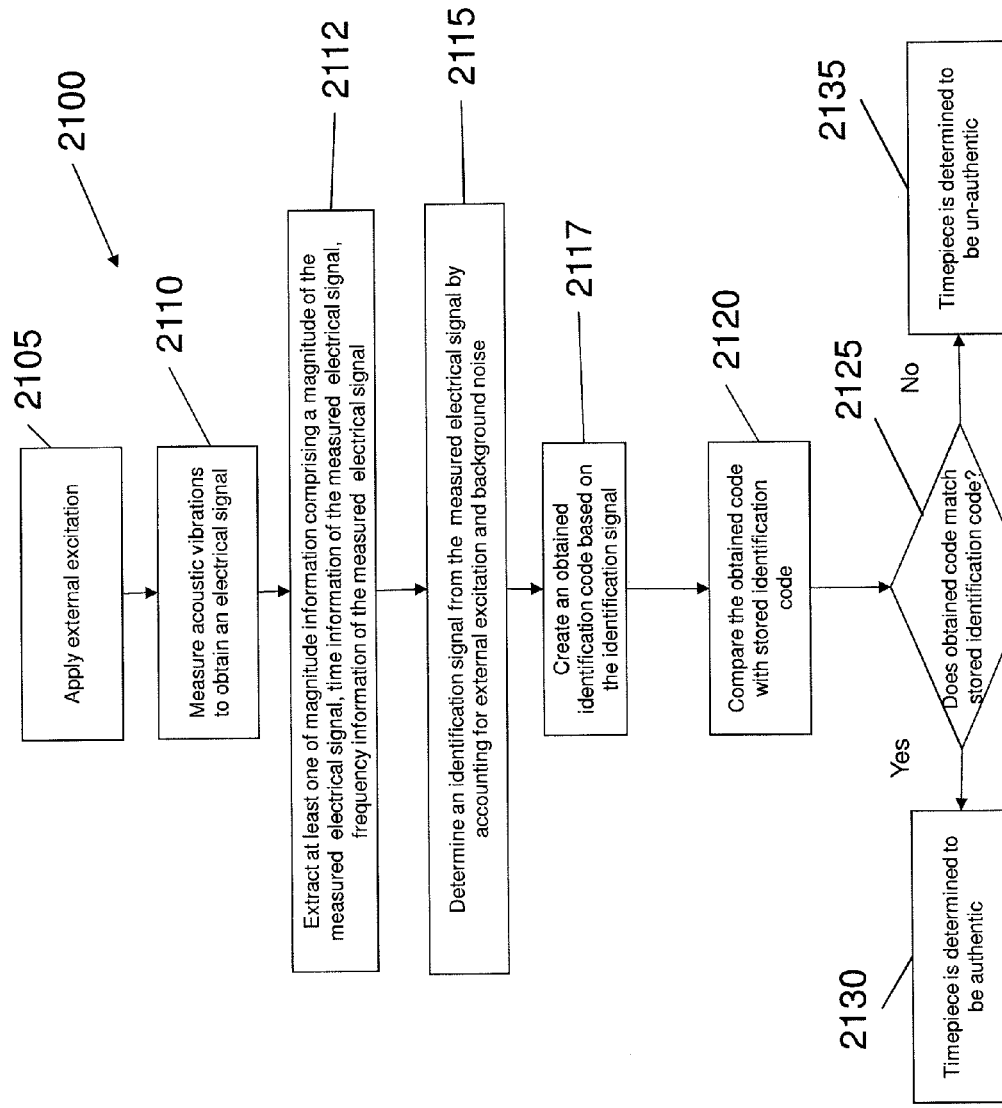

FIGS. 9 and 10 show exemplary flows for performing aspects of embodiments of the present invention. The steps of FIGS. 9 and 10 may be implemented in the environment of FIG. 8, for example. The flow diagrams may equally represent high-level block diagrams of embodiments of the invention. The flowcharts and/or block diagrams in FIGS. 9 and 10 illustrate the architecture, functionality, and operation of possible implementations of systems, methods and computer program products according to various embodiments of the present invention. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. Each block of each flowchart, and combinations of the flowchart illustrations can be implemented by special purpose hardware-based systems that perform the specified functions or acts, or combinations of special purpose hardware and computer instructions and/or software, as described above. Moreover, the steps of the flow diagrams may be implemented and executed from either a server, in a client server relationship, or they may run on a user workstation with operative information conveyed to the user workstation. In an embodiment, the software elements include firmware, resident software, microcode, etc.

Furthermore, the invention can take the form of a computer program product accessible from a computer-usable or computer-readable medium providing program code for use by or in connection with a computer or any instruction execution system. The software and/or computer program product can be implemented in the environment of FIG. 8. For the purposes of this description, a computer-usable or computer readable medium can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable storage medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disc—read/write (CD-R/W) and DVD.

FIG. 9 illustrates an exemplary flow 2000 for creating and storing an identification code for a timepiece. At step 2002, the input signal control tool controls the excitation device to apply an external excitation to a timepiece. At step 2005, the measuring tool measures acoustic vibrations to obtain an electrical signal. At step 2010, the extraction tool extracts from said electrical signal or from a representation of said electrical signal in a time or time-frequency domain at least one of: magnitude information on a magnitude of the measured electrical signal, time information of the measured electrical signal, and frequency information on a frequency of the measured electrical signal. At step 2013, the extraction tool determines an identification signal from the measured electrical signal by accounting for a signal portion based on the external excitation and accounting for a signal portion based on background noise. At step 2015, the identification tool creates an identification code or a representation based on the identification signal. At step 2020, the identification tool stores the identification code or the representation in a storage system, e.g., a database. In embodiments, the representation may comprise a picture of the signal for a comparison basis.

FIG. 10 illustrates an exemplary flow 2100 for authentication and/or identification of a timepiece. As shown in FIG. 10, at step 2105, the input signal control tool controls the excitation device (or exciter) to apply an external excitation to a timepiece. As step 2110, the measuring tool controls a microphone to measure acoustic vibrations to obtain an electrical signal. At step 2112, the extraction tool extracts from said electrical signal or from a representation of said electrical signal in a time or time-frequency domain at least one of: magnitude information on a magnitude of the measured electrical signal, time information of the measured electrical signal, and frequency information of the measured electrical signal. At step 2115, the extraction tool determines an identification signal from the measured electrical signal by accounting for a signal portion based on the external excitation and accounting for a signal portion based on background noise At step 2117, the identification tool creates an obtained identification code based the identification signal. At step 2120, the comparison tool (or comparator) compares the obtained code with stored identification codes. At step 2125, the authentication determination tool determines whether the obtained code matches a stored identification code. If, at step 2125, the authentication determination tool determines that the obtained code matches a stored identification code, at step 2130, the timepiece is determined to be authentic. If, at step 2125, the authentication determination tool determines that the obtained code match does not match a stored identification code, at step 2135, the timepiece is determined to be un-authentic.

While the invention has been described with reference to specific embodiments, those skilled in the art, will understand that various changes may be made and equivalents may be substituted for elements thereof without departing from the true spirit and scope of the invention. In addition, modifications may be made without departing from the essential teachings of the invention.

What is claimed is:

1. A method for authenticating a timepiece comprising:
applying at least one external excitation to said timepiece using an external device;
measuring acoustic vibrations at least one of emitted and absorbed inside the timepiece to obtain an electrical signal representative of the measured acoustic vibrations, wherein a magnitude of the electrical signal represents magnitude information of the measured acoustic vibrations as a function of time;
comparing the magnitude information with at least one reference magnitude information; and
determining the authenticity of said timepiece based on the comparing.

2. The method of claim 1, wherein the at least one external excitation generates at least one acoustic vibration inside the timepiece.

3. The method according to claim 1, wherein the external device comprises at least one of a transducer and a striking element.

4. The method according to claim 3, wherein the transducer comprises at least one of a piezoelectric device and a tuning fork.

5. The method according to claim 3, wherein the striking element comprises at least one of a clapper and a striker.

6. The method according to claim 1, wherein the at least one external excitation comprises at least one of regular vibrations, sequential vibrations, time-varied vibrations, intensity-varied vibrations, and pulsed vibrations, a continuous vibration with discontinuous frequencies.

7. The method according to claim 1, wherein the measuring of the acoustic vibrations emitted inside the timepiece to obtain the electrical signal comprises converting the acoustic vibrations captured by a microphone.

8. The method according to claim 1, further comprising storing the electrical signal in a database as a reference signal.

9. The method according to claim 1, further comprising processing the electrical signal by a mathematical algorithm to convert the electrical signal to a frequency or time-frequency domain.

10. The method according to claim 9 wherein the mathematical algorithm is selected from one of a Fourier transformation, a short-time Fourier transform, a Gabor transform, a Wigner transform, and a wavelet transform.

11. The method according to claim 1, wherein the measuring of the acoustic vibrations emitted inside the timepiece occurs when the timepiece is not running.

12. The method according to claim 1, wherein the measuring of the acoustic vibrations emitted inside the timepiece occurs when the timepiece is running.

13. The method according to claim 1, wherein the applying the at least one external excitation is synchronous with a tic/tock noise emanated by the timepiece, which is running.

14. The method according to claim 1 wherein the measuring of the acoustic vibrations emitted inside the timepiece occurs when at least one of a tic movement and a tock movement of the timepiece occurs.

15. The method according to claim 1 wherein the measuring of the acoustic vibrations emitted inside the timepiece occurs between occurrences of a tic movement and a tock movement of the timepiece.

16. The method according to claim 1, wherein the at least one external excitation comprises acoustic vibrations.

17. The method of claim 16, where the acoustic vibrations comprise at least one of a single tone, two or more tones, a sweep, a white noise, a colored noise, a random or pseudo-random sequence, one impulse, and a sequence of two or more impulses.

18. The method according to claim 16, wherein the at least one external excitation is continuous.

19. The method according to claim 16, wherein the external excitation is pulsed.

20. The method according to claim 19, wherein pulses of the external excitation are identical copies of one another.

21. The method according to claim 19, wherein pulses of the external excitation are different from one another.

22. The method according to claim 1, wherein the measuring of the acoustic vibrations emitted inside the timepiece at least partially overlaps in time with the at least one external excitation.

23. The method according to claim 1, wherein the measuring of the acoustic vibrations emitted inside the timepiece does not overlap in time with the external excitation.

24. The method according to claim 1, further comprising:
measuring at least one background vibration when no external excitation is applied; and
subtracting the at least one background vibration from the measured acoustic vibrations.

25. The method according to claim 1, wherein the at least one reference magnitude information comprises at least one of previously recorded data and a model.

26. The method according to claim 25, wherein the model comprises data expected based on previous observations of one or more timepieces similar to the timepiece.

27. The method according to claim 1, further comprising issuing a signal indicating one of authenticity of the timepiece and non-authenticity of the timepiece.

28. The method of claim 27, wherein the signal comprises at least one of: an alert, a hold signal, an alarm, and a notification.

29. The method according to claim 1, further comprising applying a specific excitation frequency to excite a resonator within the timepiece to extract a unique identifier for the timepiece.

30. A system for authenticating a timepiece comprising:
an exciter for applying at least one external excitation to said timepiece using an external device
a detector for measuring acoustic vibrations at least one of emitted and absorbed inside the timepiece to obtain an electrical signal representative of the measured acoustic vibrations, wherein a magnitude of the electrical signal represents magnitude information of the measured acoustic vibrations as a function of time;
a comparator for comparing the magnitude information with at least one reference magnitude information; and
an authenticator for determining an authenticity of said timepiece based on the comparing.

31. A method for creating an identifier for a timepiece comprising:
applying at least one external excitation to the timepiece using an external device;
measuring acoustic vibrations at least one of emitted and absorbed inside the timepiece to obtain an electrical signal representative of the measured acoustic vibrations; and
creating an identification code based on the electrical signal using a processor of a computing device.

* * * * *